US009719813B2

(12) United States Patent
Landis

(10) Patent No.: US 9,719,813 B2
(45) Date of Patent: Aug. 1, 2017

(54) CONNECTOR MECHANISM FOR SAFELY AND QUICKLY ATTACHING AND DETACHING A SENSOR

(71) Applicant: Scott Technologies, Inc., Boca Raton, FL (US)

(72) Inventor: Jeffrey Lynn Landis, Waxhaw, NC (US)

(73) Assignee: Scott Technologies, Inc., Boca Raton, FL (US)

( * ) Notice: Subject to any disclaimer, the term of this patent is extended or adjusted under 35 U.S.C. 154(b) by 0 days.

(21) Appl. No.: 14/843,235

(22) Filed: Sep. 2, 2015

(65) Prior Publication Data
US 2015/0377658 A1 Dec. 31, 2015

Related U.S. Application Data

(63) Continuation of application No. PCT/US2014/024004, filed on Mar. 12, 2014.
(Continued)

(51) Int. Cl.
| H01R 13/64 | (2006.01) |
| G01D 11/24 | (2006.01) |
| G01N 33/00 | (2006.01) |
| H01R 24/38 | (2011.01) |
| H01R 13/645 | (2006.01) |
| H01R 103/00 | (2006.01) |

(52) U.S. Cl.
CPC ....... G01D 11/245 (2013.01); G01N 33/0009 (2013.01); H01R 13/64 (2013.01); H01R 24/38 (2013.01); H01R 13/6456 (2013.01); H01R 2103/00 (2013.01)

(58) Field of Classification Search
CPC ............................ H01R 13/64; H01R 13/6456
USPC ......................................................... 439/680
See application file for complete search history.

(56) References Cited

U.S. PATENT DOCUMENTS

| 268,330 A | 11/1882 | Weston |
| 1,374,832 A | 4/1921 | Donle |
| (Continued) | | |

FOREIGN PATENT DOCUMENTS

| EP | 0113966 A2 | 7/1984 |
| EP | 0166209 A2 | 1/1986 |
| EP | 2466297 A2 | 6/2012 |

*Primary Examiner* — Abdullah Riyami
*Assistant Examiner* — Justin Kratt
(74) *Attorney, Agent, or Firm* — Christopher & Weisberg, P.A.

(57) ABSTRACT

A connector mechanism for safely and quickly attaching or detaching a sensor. The connector mechanism includes a sensor head assembly comprising a detector body with an internal channel, an open distal end, and a sensor head attachment connector (HAC) located within the channel. The HAC includes a first electrical connection having at least a first contact member and a first key component located in a fixed location relative to the first contact member. The connector mechanism includes a sensor cartridge comprising a cartridge housing with a probe component, a second electrical connection having at least a second contact member configured to mate with the first contact member, and a second key component that is located in a fixed location relative to the second contact member. The first and second key components engage one another before the first and second contact members engage one another.

12 Claims, 10 Drawing Sheets

Related U.S. Application Data

(60) Provisional application No. 61/781,333, filed on Mar. 14, 2013.

(56) References Cited

U.S. PATENT DOCUMENTS

| | | | |
|---|---|---|---|
| 4,395,082 A | | 7/1983 | Rumble |
| 5,338,435 A | | 8/1994 | Savage |
| 5,564,951 A | * | 10/1996 | Attal ............... A61B 5/021 |
| | | | 29/858 |
| 5,746,976 A | | 5/1998 | Shimizu |
| 2003/0109180 A1 | * | 6/2003 | Mueller ............ H01R 13/6315 |
| | | | 439/680 |
| 2003/0224643 A1 | | 12/2003 | Blatnica |
| 2009/0314056 A1 | | 12/2009 | Nelson |
| 2010/0157288 A1 | | 6/2010 | Brossette |
| 2010/0170794 A1 | | 7/2010 | Sell |
| 2013/0033841 A1 | | 2/2013 | Eckhardt |

\* cited by examiner

CONNECTOR MECHANISM FOR SAFELY AND QUICKLY ATTACHING AND DETACHING A SENSOR

CROSS-REFERENCE TO RELATED APPLICATIONS

This application is a continuation of International Patent Application No. PCT/US2014/024004 filed Mar. 12, 2014, which claims priority to and the benefit of the filing date of U.S. Provisional Application No. 61/781,333, filed on Mar. 14, 2013, both of which are incorporated herein by reference in their entirety.

BACKGROUND

The subject matter described herein relates generally to sensors, and particularly to attaching and detaching a sensor cartridge from a sensor head assembly.

Environmental sensing systems may include a variety of sensors for detecting the presence and/or concentration of various chemicals in hazardous environments. For example, sensors may be used in hazardous environments for detecting the presence and/or concentration of hazardous (e.g., combustible) and/or toxic gases.

The sensing systems generally include a sensor housed in a cartridge and a head assembly coupled to a mounting structure. The head assembly provides a removable electrical interface between a sensor and the mounting structure. The sensor generally includes an interface having a pin array to removably couple to the head assembly. However, the interface requires manual alignment of the pin array such that the sensor cartridge cannot be mated to the head assembly in a blind fashion (e.g., an operator has to visual inspect and ascertain the orientation of the pin array to align the sensor to the head assembly). Furthermore, because the pin array is not guarded, pins may be damaged as the operator attempts to properly align the pin array.

SUMMARY

The subject matter described herein relates to a connector mechanism for safely and quickly attaching or detaching a sensor. The connector mechanism includes a sensor head assembly comprising a detector body with an internal channel and an open distal end. The connector mechanism also includes a sensor head attachment connector (sensor HAC) located within the channel. The HAC may be oriented to face the distal end and recessed within the channel remote from the distal end. The HAC may include a first electrical connection having at least a first contact member. The HAC may include a first key component that is located in a fixed location relative to the first contact member. The connector mechanism also includes a sensor cartridge comprising a cartridge housing that includes a probe component. The sensor cartridge may be configured to be at least partially inserted through the open distal end into the internal channel of the detector body. The sensor cartridge may also include a second electrical connection having at least a second contact member configured to mate with the first contact member. The sensor cartridge may also include a second key component that is located in a fixed location relative to the second contact member. The first and second key components engage one another before the first and second contact members engage one another.

BRIEF DESCRIPTION OF THE DRAWINGS

The drawings, in which like numerals represent similar parts, illustrate generally, by way of example, but not by way of limitation, various embodiments discussed in the present document.

DETAILED DESCRIPTION

Figure 1:
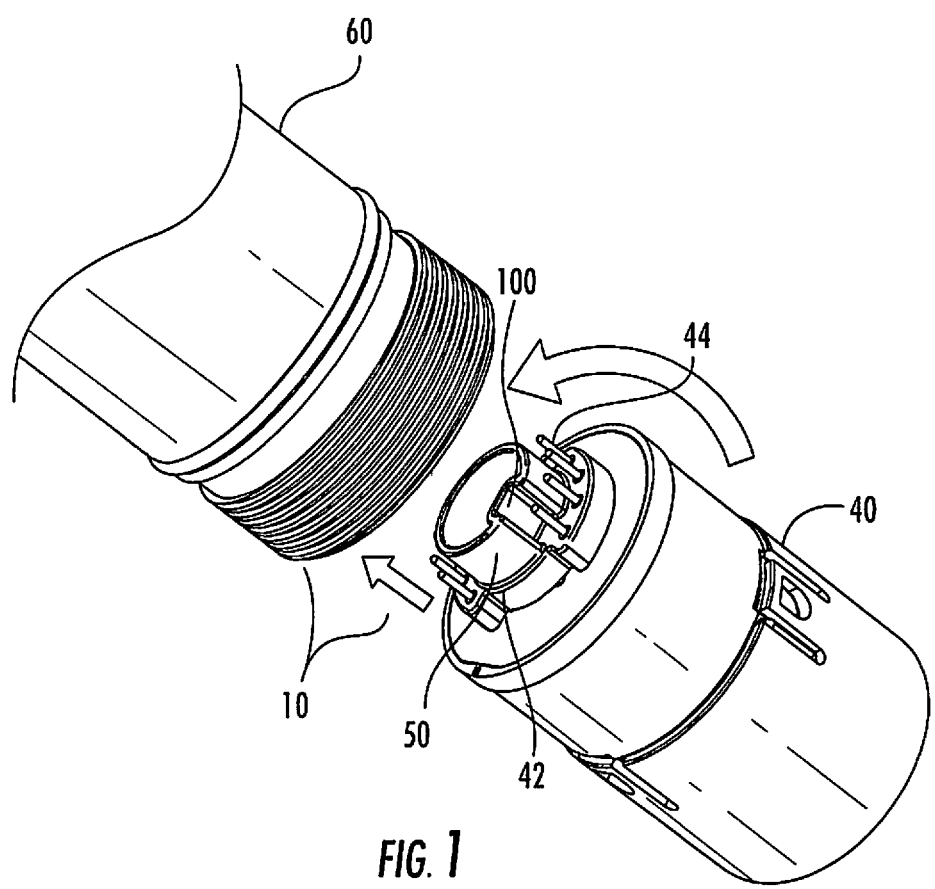
FIG. 1 is an illustration of the insertion of a sensor connector into the sensor head channel for attaching the sensor to the sensor head.
Figure 2:
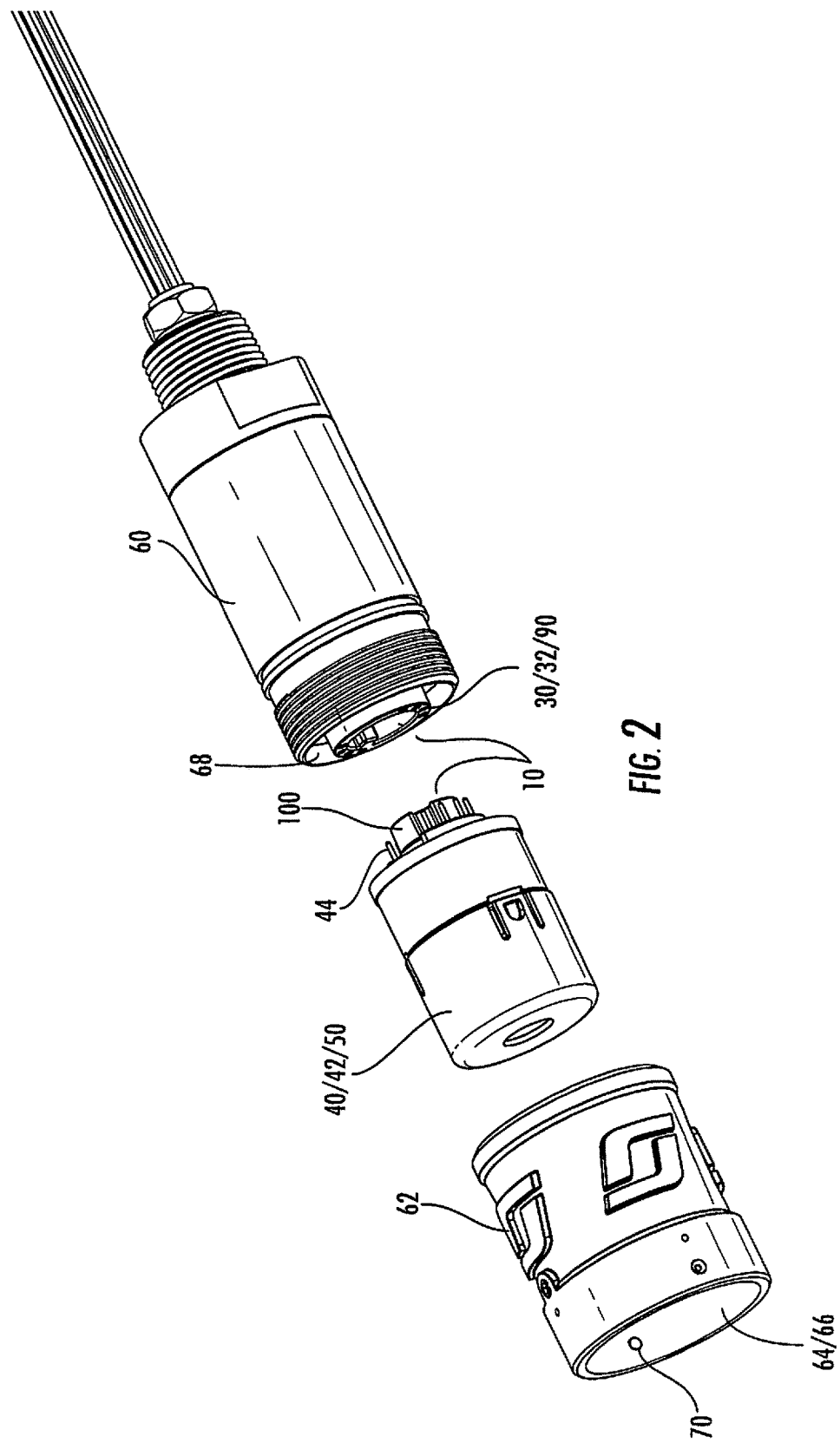
FIG. 2 is an expanded representation of the sensor head assembly with the sensor and retaining cap.

As seen in FIGS. 1 and 2, a connector mechanism 10 for safely and quickly attaching or detaching a sensor or sensor assembly 40 to a sensor head assembly 60. The sensor head assembly 60 has a sensor retaining cap 62 with an opening 66 which exposes the sensor to the atmosphere. The sensor retaining cap cavity 64 is equipped with two bayonet pins 70 for quarter turn sensor head accessories such as but not limited to calibration adapter, water deluge guard, and positive flow thru adapter. A sensor head attachment connector 30 resides within the sensor head channel 68 and is accessible when the sensor retaining cap is removed from the sensor head assembly 46.

As further seen in the figures, the sensor head attachment connector 30 has a first electrical connection 32 that contains at least one electrical connection 32, preferably multiple electrical connections 32, e.g., 2, 3 4, 5, 6, 7, 8, 9 or any other number of electrical connections 32 as desired. A first key component 90 is also part of the sensor head attachment connector 30, with the first key component 90 in the fixed location relative to the first electrical connection 32. As such, the first electrical connection 32 remains in a permanent position relative to the first key component 90 regardless of the movement of the first key component 90. Additionally, the first electrical connection 32 is recessed relative to the first key component 90, or stated differently, the first key component 90 is raised above the first electrical connection 32. Preferably the first key component 90 is a continuous solid configuration, such as circular, oval rectangular, diamond, square, or other form, that permits, and is readily maneuvered to, insertions into or outside of a receiving shape. In one embodiment, the first key component 90 is inserted into a second key component 100 or receiving shape. In another embodiment, the first key component 90 that can be inserted into a receiving shape 100 has a solid interior area. The first electrical connection 32 may be located within and/or outside of the first key component 90.

Referring again to the figures, the sensor component 40 includes a second housing 42 having a probe component 50. Additionally, the sensor 40 has a second electrical connection 44 configured to mate with the first electrical connection 32. The second key 100 is located on the sensor 40 and is in a fixed location relative to the second electrical connection 44, with the second electrical connection 44 is recessed relative to the second key component 100. As such, the second electrical connection 44 remains in a permanent position relative to the second key component 100 regardless of the orientation or movement of the second key component 100. Additionally, the second electrical connection 44 is recessed relative to the second key component 100, or stated differently, the second key component 100 is raised above the second electrical connection 44. The second key component 100 is preferably a continuous solid configuration, and configured in such a manner as to mate with the first key component 90 in such a manner as to be readily maneuvered to, insertions into or outside of the first key component 90. In one embodiment, the second key component 100 is inserted into the first key component 90. In another embodiment, the second key component 100 can be inserted into the first key component 90 and has a solid interior area. The second electrical connection 44 may be located within and/or outside of the second key component 100 as it is placed in a position relative to the second key component 100 as to engage the first electrical connection 32 when the first 90 and second key components 100 are mated. As such, the second key component 100 is configured to interlock with the first key component 90, but the first 32 and second 44 electrical connections are longitudinally blocked from engaging each other until the first 90 and second 100 keys components are aligned.

As seen in FIG. 1, the connector mechanism 10 is particularly useful for hot swapping sensors in explosive environments.

In operation, referring to FIG. 2, the sensor probe component 50 fits within the sensor head cavity 68 for connection of the first 90 and second 100 keys components and first 32 and second 44 electrical connections with such reduced angular movement from the longitudinal axis of the channel 90 and probe 50 component that the first electrical connection 32 does not contact any member of the sensor 40 and the second electrical connection 44 does not contact any member of the sensor head attachment connector 30 prior to the first 90 and second 100 key components engaging each other. As the probe 50 is inserted into the sensor head channel 68, the first 90 and second 100 key components come into longitudinal contact with each other which prohibits further insertion of the probe 50 into the sensor head channel 68. The probe 50 is rotated or twisted in its longitudinally blocked position until the first key component 90 and second key component 100 are aligned. Once the first 90 and second 100 key components are aligned, the probe 50 can be further inserted into the sensor head channel 68 such that the first 90 and second 100 key components continue to engage each other. With the sensor 40 and sensor head assembly 60 aligned, as the first 90 and second 100 key component continue to engage, the first 32 and second 44 electrical connections are aligned for insertion into one another. Once the first 90 and second 100 key components are fully engaged, the longitudinal insertion of the probe 50 is blocked and the first 32 and second 44 electrical connections are now fully connected.

The subject matter described herein is particularly useful in sensor applications where the sensor is guided in the detector head housing and the connection is made in a blind, i.e., where the person inserting the sensor head do not have any visual indication of the proper line of insertion of the sensor head. The two surfaces of the plug and socket (the first and second key components) act like a bearing surface allowing the sensor to rotate until the sensor key and socket keyway align sliding together allowing the electrical connection components, preferably eight (8) contacts, to mate. The subject matter described herein is particularly useful in gas sensor and/or hot swappable detector head designs.

Figure 3:
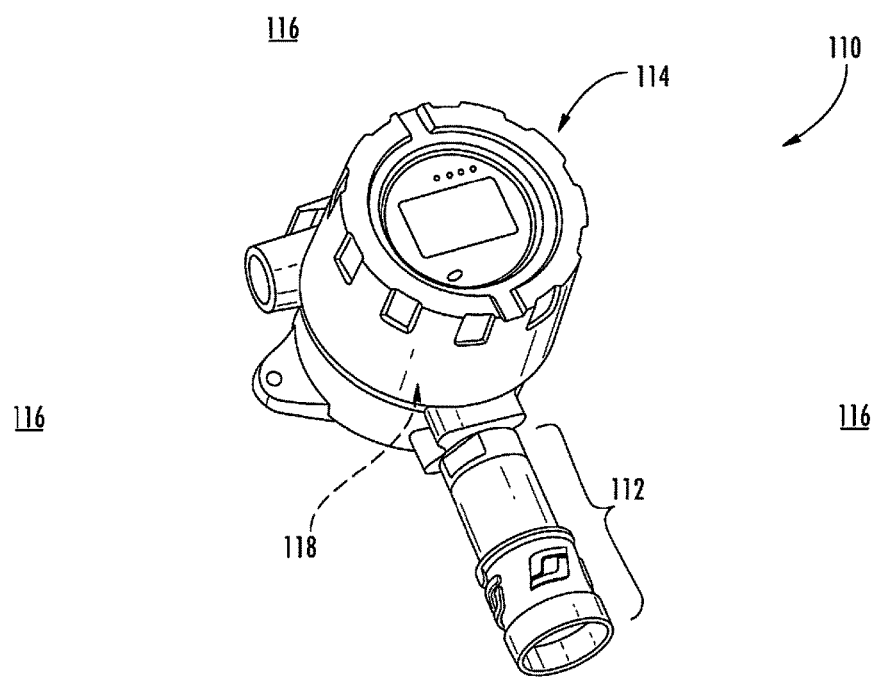
FIG. 3 is a perspective view of an embodiment of a sensor assembly.

FIG. 3 is a perspective view of an embodiment of a sensor assembly 110. The sensor assembly 110 includes a sensor 112 and a mounting structure 114. As shown in FIG. 3, the sensor 112 is mounted to the mounting structure 114 such that the sensor 112 is exposed within an environment 116 for sensing one or more parameters within the environment 116. The sensor 112 may be any type of sensor that is configured to sense any parameter(s). For example, in some embodiments, the sensor 112 is configured to detect the presence and/or amount of a substance (e.g., a volatile gas and/or the like) within the environment 116. Examples of other parameters that may be sensed by the sensor 112 include, but are not limited to, pressure, density, temperature, relative humidity, and/or the like. The sensor 112 may be used in any application and the environment 116 may be any environment. In some embodiments, the environment 116 is a hazardous environment, such as, but not limited to, a petroleum well, a power plant, a petroleum pipe system, and/or the like. For example, the sensor 112 may be used within a hazardous environment for detecting the presence and/or amount of a volatile gas within the hazardous environment.

The mounting structure 114 supports the sensor 112 such that the sensor 112 is exposed within the environment 116 for performing sensing operations. The mounting structure 114 may include any structure, means, configuration, and/or the like that enables the mounting structure 114 to support the sensor 112 within the environment 116. In some embodiments, the mounting structure 114 is merely a panel and/or wall to which the sensor 112 is mounted, while in other embodiments the mounting structure 114 may include processing components, power supply components, communications components, and/or the like that support operation of the sensor 112. For example, the mounting structure 114 may hold one or more electrical power sources (not shown; e.g., a battery and/or the like) and/or one or more electrical power distribution components (not shown; e.g. electrical wires and/or cables, circuit boards, switches, relays, transformers, capacitors, voltage regulators, current regulators, and/or the like) for supplying electrical power to the sensor 112 to power operation of the sensor 112. The mounting structure 114 may hold one or more processing components (not shown; e.g., computers, processors, controllers, microprocessors, circuit boards, microcontrollers, memories, integrated circuits, and/or the like) that process signals from the sensor 112 that represent the parameter(s) sensed by the sensor 112. Processing of signals from the sensor 112 optionally includes data logging operations. In addition or alternative to the power supply component(s) and/or the processing component(s), the mounting structure 114 may hold one or more communication components (not shown; e.g., electrical wires and/or cables, circuit boards, other electrical pathways, switches, relays, communication nodes, and/or the like) that enables the sensor 112 to communicate with a remote location and/or other sensors. The remote location and/or the other sensors may contain one or more processing components and/or electrical power components that relate to operation of the sensor 112.

Optionally, the mounting structure 114 may include an interior chamber that is hermetically sealed to separate a volume of space within the mounting structure 114 from the environment 116. For example, in the illustrated embodiment, the mounting structure 114 is an explosion-resistant housing having an interior chamber 118 that holds one or more processing components, power supply components, and/or communication components that relate to operation of the sensor 112. The interior chamber 118 is separated from the environment 116 such that any combustion and/or explosion within the interior chamber 118 is less likely to extend into the environment 116. As such, any combustion and/or explosion that occurs within the interior chamber 118 is less likely to cause any substance within the environment to combust and/or explode. The illustrated embodiment of the mounting structure 114 may be commonly referred to as an "explosion-proof transmitter enclosure." Although described above as being an active sensor that requires a supply of electrical power to operate, the sensor 112 may be a passive sensor that does not require a supply of electrical power to operate.

Figure 4:
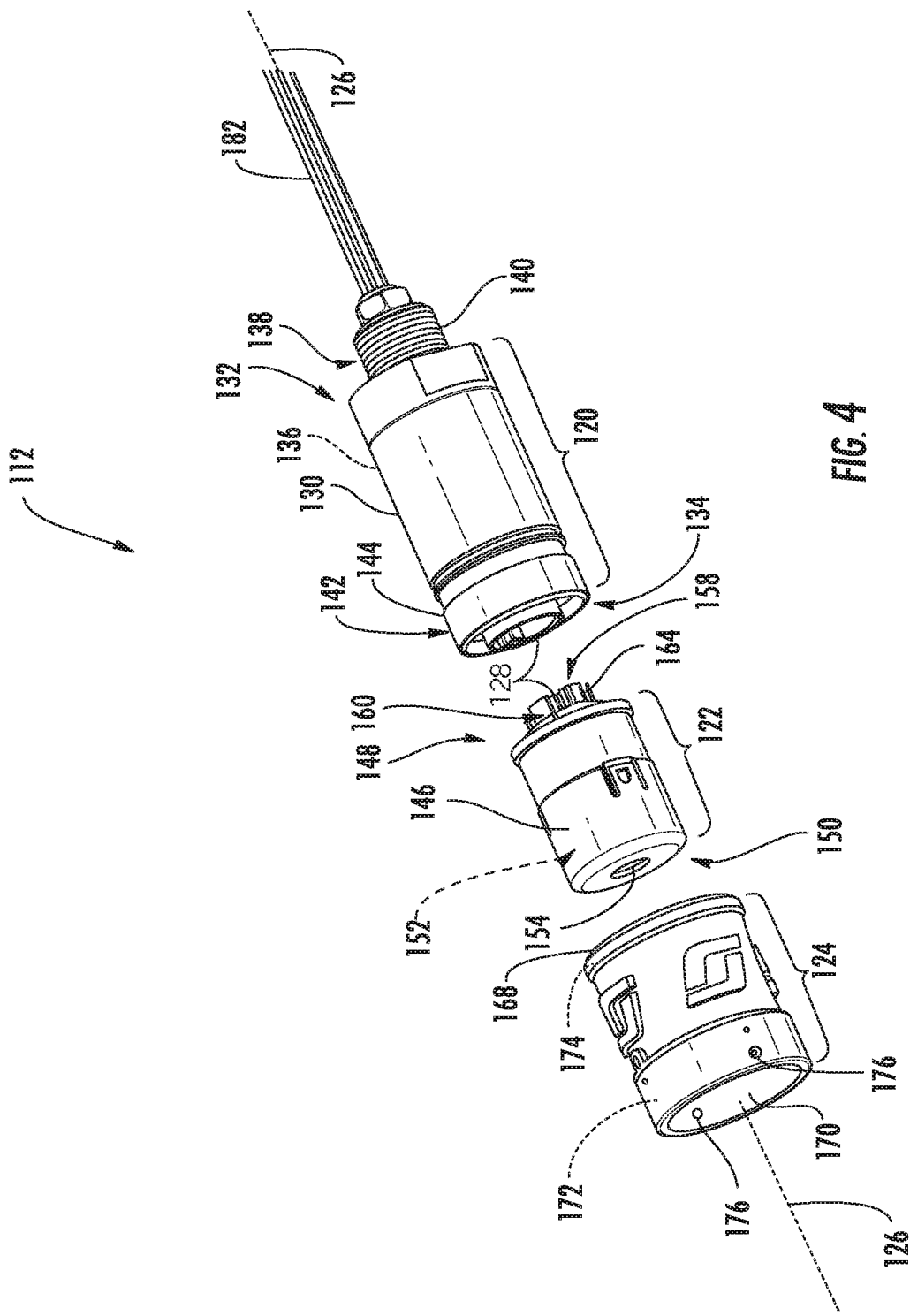
FIG. 4 is an exploded perspective view of an embodiment of a sensor of the sensor assembly shown in FIG. 3.

FIG. 4 is an exploded perspective view of an embodiment of the sensor 112 shown in FIG. 3. The sensor 112 includes a sensor head assembly 120, a sensor cartridge 122, and a retaining cap 124. The sensor 112 is elongated and extends along a central longitudinal axis 126. The sensor head assembly 120 and the sensor cartridge 122 include a connector mechanism 128 for attaching and detaching the sensor cartridge 122 to and from the sensor head assembly 120. When the sensor cartridge 122 is attached to the sensor head assembly 120, the connector mechanism 128 electrically connects the sensor cartridge 122 to the sensor head assembly 120. The connector mechanism 128 is discussed in further detail below. The sensor head assembly 120 is then electrically connected to the mounting structure 114 via the wiring 182.

The sensor head assembly 120 includes a detector body 130. The detector body 130 extends a length along the central longitudinal axis 126 from an end 132 to an opposite end 134. The detector body 130 includes an internal channel 136 that extends through the detector body 130 along at least a portion of the length of the detector body 130. The internal channel 136 extends into the detector body 130 through the end 134 such that the end 134 is open to the internal channel 136. The end 134 will be referred to herein as an "open distal end" and as a "distal end."

The connector mechanism 128 illustrated in FIG. 4 is shown positioned flush with the open distal end 134 for illustration purposes. As discussed in further detail below, the connector mechanism 128 is recessed into the detector body 130.

The sensor head assembly 120 may include an attachment member 138 for mounting the sensor 112 to the mounting structure 114 (shown in FIG. 3). In the illustrated embodiment, the attachment member 138 includes a thread 140 for threadably connecting the sensor 112 to the mounting structure 114. But, in addition or alternatively to the thread 140, the attachment member 138 may use any other mounting strategy, such as, but not limited to, an adhesive, an interference fit, a snap-fit, a latch, a clip, a clamp, a threaded fastener, and/or the like. In the illustrated embodiment, the attachment member 138 is located at the end 132 of the detector body 130, however, the attachment member 138 may have any other location along the detector body 130.

The sensor head assembly 120 may include an attachment member 142 for mounting the retaining cap 124 to the detector body 130. The illustrated embodiment of the attachment member 142 includes a thread 144 that enables the retaining cap 124 to be mounted to the detector body 130 by being threadably connected to the detector body 130. In addition or alternatively to the thread 144, the attachment member 142 may use any other mounting strategy for mounting the retaining cap 124 to the detector body 130, such as, but not limited to, an adhesive, an interference fit, a snap-fit, a latch, a clip, a clamp, a threaded fastener, and/or the like. Although the attachment member 142 is shown as being formed at the end 134 of the detector body 130, the attachment member 142 may have any other location along the detector body 130. The structure and function of the retaining cap 124 will be discussed below.

The sensor cartridge 122 includes a cartridge housing 146 that extends a length along the central longitudinal axis 126 from an end 148 to an opposite end 150. The cartridge housing 146 includes an interior chamber 152. The sensor cartridge 122 includes a sensing element (not shown) that is held within the interior chamber 152 of the cartridge housing 146. The sensing element is configured to sense one or more parameters from the environment 116 (shown in FIG. 1). The sensing element may be any type of sensing element that is configured to sense the parameter(s) in any manner. In the illustrated embodiment, the sensing element is a diffusion type sensing element that senses the parameter(s) through diffusion. The cartridge housing 146 includes a diffusion opening 154 that exposes the sensing element to the environment 116 to enable the sensing element to sense the parameter(s) through diffusion. Although shown as extending through the end 150 of the cartridge housing 146, the diffusion opening 154 may be positioned at any other location along the cartridge housing 146 that enables the sensing element to sense the parameter(s). Although only one is shown, the cartridge housing 146 may include any number of diffusion openings 154. Any other type of sensing element may be used in addition or in alternative to the diffusion type sensing element described herein.

As briefly discussed above, the sensor head assembly 120 and the sensor cartridge 122 include the connector mechanism 128. Specifically, the sensor head assembly 120 includes a sensor head attachment connector (sensor HAC) 156 of the connector mechanism 128 and the sensor cartridge 122 includes a probe component 158 of the connector mechanism 128. The sensor HAC 156 and the probe component 158 are configured to mate together to electrically connect the sensor cartridge 122 to the sensor head assembly 120. The sensor HAC 156 is located within the internal channel 136 of the detector body 130. The cartridge housing 146 is configured to be at least partially inserted into the internal channel 136 to mate the probe component 158 and the sensor HAC 156 to one another. As will be discussed below in more detail, the probe component 158 includes a key component 160 that is configured to cooperate and interlock with a key component 162 of the sensor HAC 156 to ensure contact members 164 of the probe component 158 engage corresponding contact members 166 of the sensor HAC 156 only when the key components 162 and 160 are properly aligned with one another. The key component 160 may be referred herein as a "second key component," while the key component 162 may be referred to as a "first key component." Each of the contact members 164 may be referred to herein as a "second contact member," and each of the contact members 166 may be referred to herein as a "first contact member."

The retaining cap 124 extends a length along the central longitudinal axis 126 from an end 168 to an opposite end 170. The retaining cap 124 includes an interior passage 172 that extends through the length of the retaining cap 124. The retaining cap 124 is configured to be mounted to the detector body 130. When mounted to the detector body 130, the retaining cap 124 extends at least partially around the sensor cartridge 122 for protecting the sensor cartridge 122 from damage (e.g., impact damage). The sensing element of the sensor cartridge 122 is exposed to the environment 116 through the internal passage 172, which is open to the environment 116 at the end 170. The interior passage 172 optionally includes a screen (not shown) to facilitate preventing debris from entering the interior passage 172 and possibly fouling the sensor element.

The retaining cap 124 includes an attachment member 174 for mounting the retaining cap 124 to the detector body 130. In the illustrated embodiment, the attachment member 174 includes a thread (not shown) that enables the retaining cap 124 to be mounted to the detector body 130 by threadably connecting the retaining cap 124 to the thread 144 of the detector body 130. Additionally or alternatively, the attachment member 174 may use any other mounting strategy for mounting the retaining cap 124 to the detector body 130, such as, but not limited to, an adhesive, an interference fit, a snap-fit, a latch, a clip, a clamp, a threaded fastener, and/or the like. Although the attachment member 174 is shown as being formed at the end of the retaining cap 124, the attachment member 174 may have any other location along the retaining cap 124.

Optionally, the retaining cap 124 includes an attachment member for connecting an accessory (not shown) to the sensor 112. Examples of accessories include, but are not limited to, calibration adapters, water deluge guards, positive flow-through adapters, and/or the like. In the illustrated embodiment, the retaining cap 124 includes bayonet pins 176 that connect to accessories using a bayonet-type connection. In addition or alternatively, any other type of connection may be used to connect accessories to the sensor 112.

Figure 5:
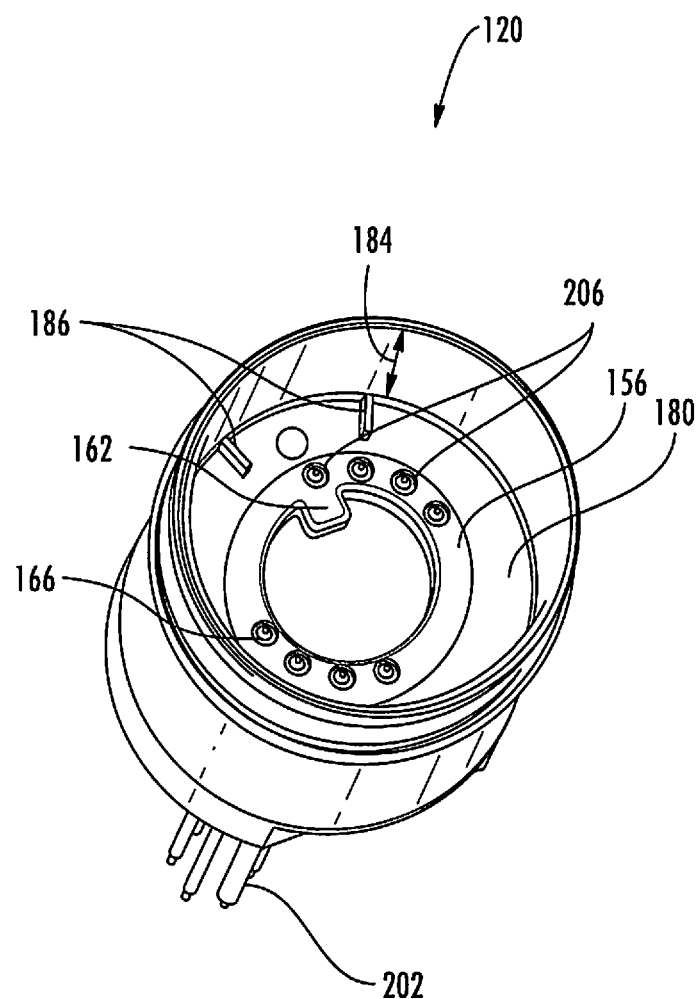
FIG. 5 is a perspective view of an embodiment of a sensor head assembly of the sensor shown in FIG. 4.

FIG. 5 is an end perspective view of an embodiment of the sensor head assembly 120 shown in FIG. 4. The sensor HAC 156 is located within the internal channel 136. The sensor HAC 156 is recessed within the internal channel 136 remote from the distal end 134 along the longitudinal axis 126. In other words, the sensor HAC 156 is positioned within the internal channel 136 a predetermined distance 184 from the distal end 134. The distance from the distal end 134 and the position of the sensor HAC is referred to herein as the "staging" distance 184 and is discussed below. The sensor HAC 156 is oriented to face the open, distal 134 end of the sensor head assembly 120. Optionally, the sensor HAC 156 can be mounted to a printed circuit board (PCB) 180 or other electronic components. The PCB 180 is then electrically connected to the wiring 182 via the electrical contact member 202 that electrically connects the sensor 112 to processing components, power supply components, communication components, and/or the like that support operation of the sensor 112. In the illustrated embodiment, the sensor HAC 156 is shown as having a cylindrical shape, however, the sensor HAC 156 may include any shape.

The sensor HAC 156 includes a first electrical connection 206 that provides an electrical connection between the wiring 182 and the sensor cartridge 122. The sensor HAC 156 also includes one or more first contact members 166 arranged circumferentially about a core area. The first contact member 166 may be located in a fixed location relative to the first key component 162. The first contact member 166 provides a connection to conductively and electrically join the first electrical connection 206 in the sensor HAC 156 to the second electrical 144 connection in the sensor cartridge 122. Accordingly, the first contact member 166 may join the second contact member 164 to the wiring 182. The wiring 182 may then electrically join the sensor assembly 112 to processing and/or power components within the interior chamber 118 of the mounting structure 114. The first contact member 166 may include one or more electrical connections (e.g., 1, 2, 3, 4, 5, 6, 7, or 8) as desired. In the illustrated embodiment, the first contact member 166 is configured as a contact receptacle configured to receive the second contact member 164 that is pin shaped. Optionally, the first contact member 166 and the second contact member 164 could be any compatible shape to provide an electrical connection.

The sensor HAC 156 includes the first key component 162. The first key component 162 is located in a fixed location relative to the first contact member 166. The first key component 162 is located on the sensor HAC 156 and the corresponding second key component 160 is located on the sensor probe component 158. Although shown as a standoff in the illustrated embodiment, the key components may be any set of compatible mating features. For example, the first key component 162 may be a protrusion oriented to extend toward the open distal end 134 and aligns with a recess or groove in the probe component 158. Alternatively the first key component 162 may be a continuous solid configuration, such as circular, oval rectangular, diamond, square, trapezoidal, or other shape configured to align and mate with the second key component 160 that may be a negative image of the shape of the first key component 162.

Optionally, the sensor head assembly 120 may include additional key components 186 within the internal channel 136. The additional key components 186 may be a standoff extending radially inward within the internal channel 136. In the illustrated embodiment, the additional key components 186 are shown as standoffs extending radially inward toward the central axis 126. However, the additional key components 186 may be any member that at least partially circum-navigates the internal perimeter of the internal channel 136. The additional key components 186 may be positioned in a fixed location relative to the contact members and are configured to engage with a second additional key component on the probe component 158, as discussed below.

Figure 6:
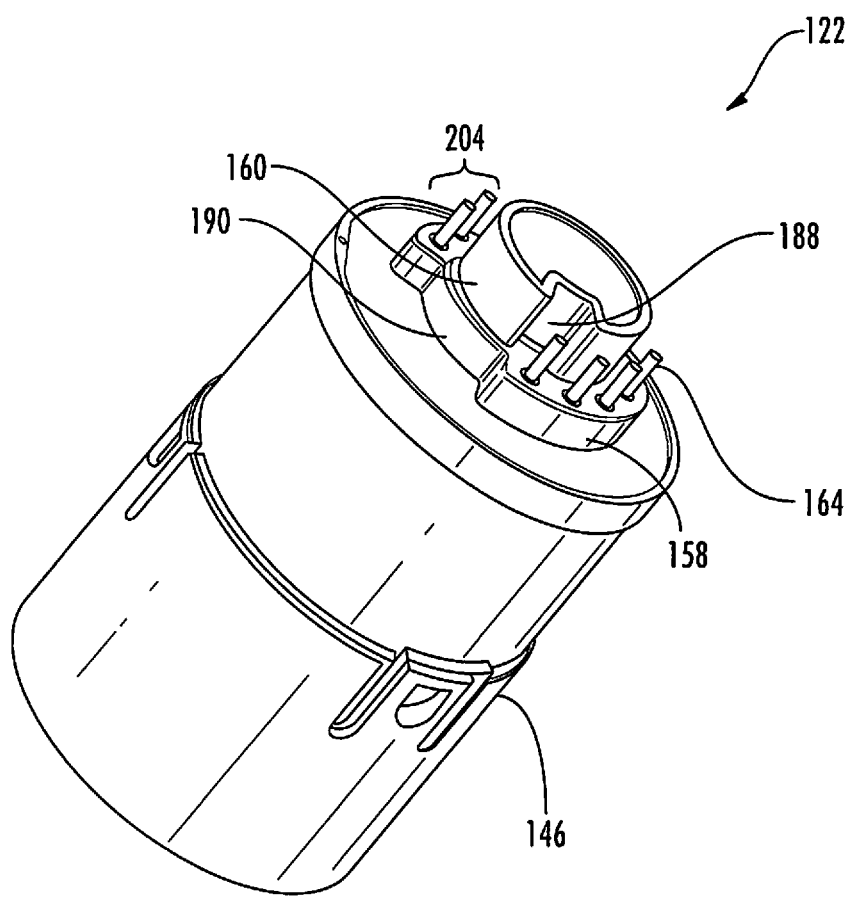
FIG. 6 is a perspective view of an embodiment of a sensor cartridge of the sensor shown in FIG. 4.

FIG. 6 is a perspective view of an embodiment of the sensor cartridge 122 shown in FIG. 4 to better illustrate the probe component 158. The probe component 158 is configured to mate with the sensor HAC 156 and provide an electrical connection between the sensor cartridge 122 and the sensor head assembly 120 via the second electrical connection 204. Accordingly, the probe component 158 includes at least one of the second contact members 164 within the second electrical connection 204, which is configured to mate with the corresponding first contact member 166 in the first electrical connection 206. In the illustrated embodiment, the second contact member 164 is a pin and the first contact member 166 is a receptacle, however, any electrically mating member pair may be used. For example, the contact member 166 and 164 may be rectangular contact pads configured to abut against one another to form an electrical connection between the contact pads.

The sensor probe component 158 includes a second key component 160. The second key component 160 is located in a fixed location relative to the contact member 164. As shown in the illustrated embodiment, the second key component 160 includes a groove 188 that receives the standoff 162. Also shown in the illustrated example, the probe component 158 includes an optional base key 190 that cooperates (e.g., sized and shaped to receive) with the alternate key component 186 of the sensor HAC 156.

Figure 7:
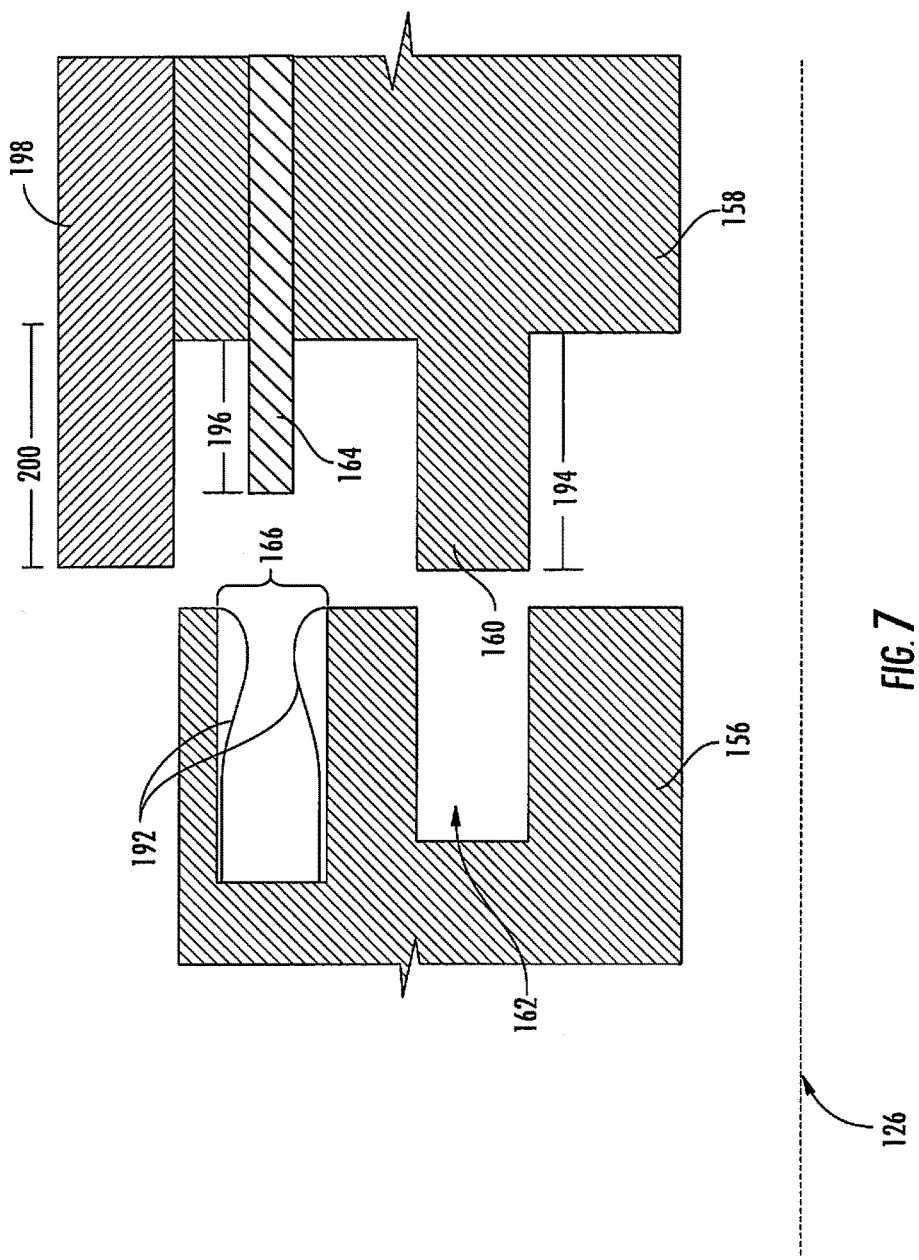
FIG. 7 is a cross-sectional view of an embodiment of a sensor head attachment connector and the sensor probe shown in FIG. 4.

FIG. 7 is a cross-sectional view of a portion of the sensor HAC 156 and the sensor probe component 158 aligned with one another, but spaced apart along the longitudinal axis 126 such that the sensor HAC 156 and the probe component 158 have not mated (e.g. do not touch or abut one another). As discussed in detail below, the sensor cartridge 122 may be rotated within the internal channel 118 about the longitudinal axis 126 until the key component 162 aligns with the key component 160, to achieve the orientation illustrated. Additionally, the second key component 160 is shown aligned with the first component 162, and the contact member 164 is aligned with the contact member 166.

In the illustrated example, the contact member 166 is configured as a receptacle (e.g., a right circular cylindrical cavity). The contact member 166 includes at least one spring-loaded contact elements 192 situated along the internal perimeter of the contact member 166. To electrically couple the sensor cartridge 122 with the sensor HAC 120, the contact pin 164 may be inserted into the contact member 166 by moving the sensor cartridge 122 along the longitudinal axis 126 toward the sensor HAC 120. When inserted, the spring-loaded contact elements 192 exerts a compressive force upon the contact member 166 providing a friction fit and electrical contact.

The second key component 160 may extend a key length 194 outward from the sensor probe component 158 along the longitudinal axis 126. Similarly, the contact member 164 may extend a contact length 196 outward from the sensor probe component 158 along the longitudinal axis 126. As shown, the key length 194 is greater than the contact length 196. The key length 194 is greater than a contact length 196 to allow the second key component 160 to contact a surface (e.g., the surface of the HAC) before the contact pin 164 can contact a surface. Accordingly, the second key component 160 engages the first key component 162 before the second contact member 164 engages the first contact member 166.

Optionally, the probe component 158 may include a shroud component 198. The shroud component 198 may be an extension of the probe component 158 that is located a fixed location relative to the contact member 160. The shroud component 198 may extend along the longitudinal axis 126 toward the distal end of the sensor cartridge 122. Similar to the second key component 160, the shroud component 198 may extend further toward the distal end of the sensor cartridge 122 than the contact member 160. In other words, the shroud component 160 may have a shroud length 200 that is greater than the contact length 196. The shroud component 198 may protect the contact member 194 from damage (e.g., impact damage).

Figure 8:
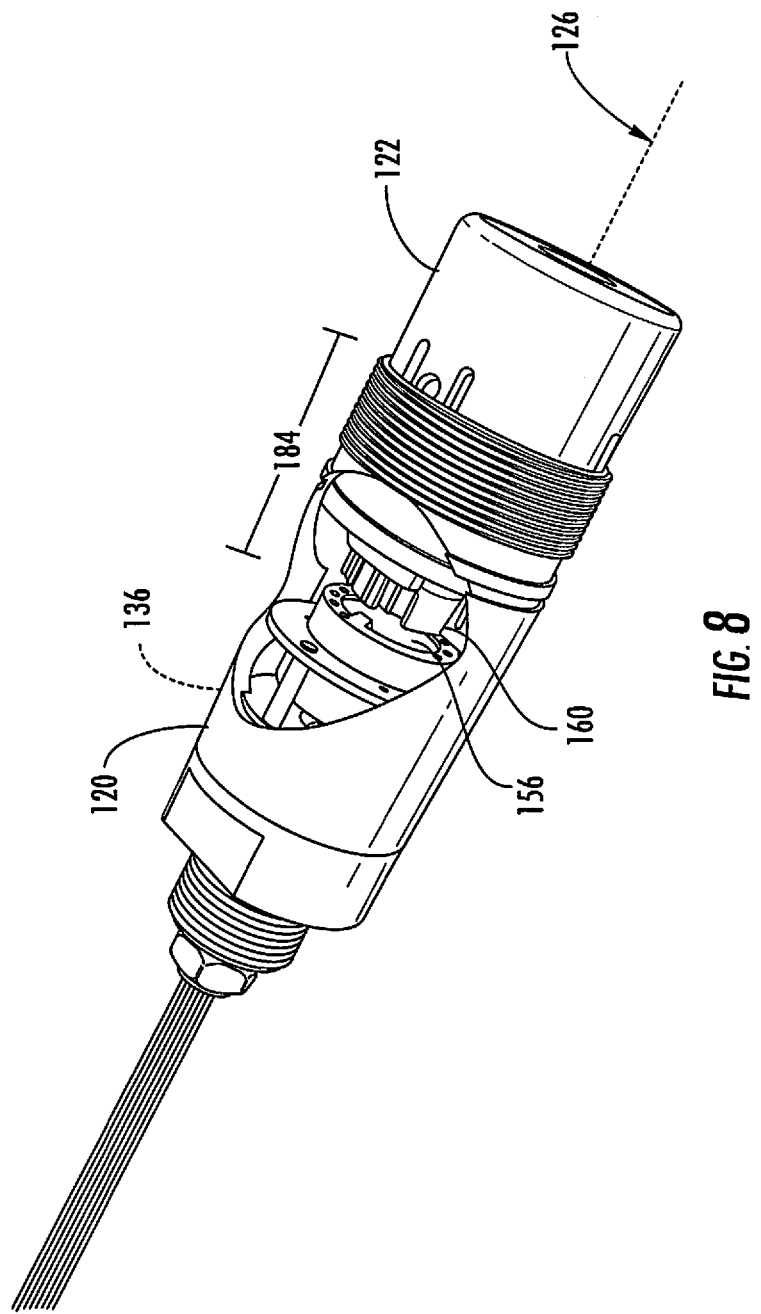
FIG. 8 is a cut-away perspective view of the sensor shown in FIG. 4 with a cut-away portion showing the head attachment connector of FIG. 7.
Figure 9:
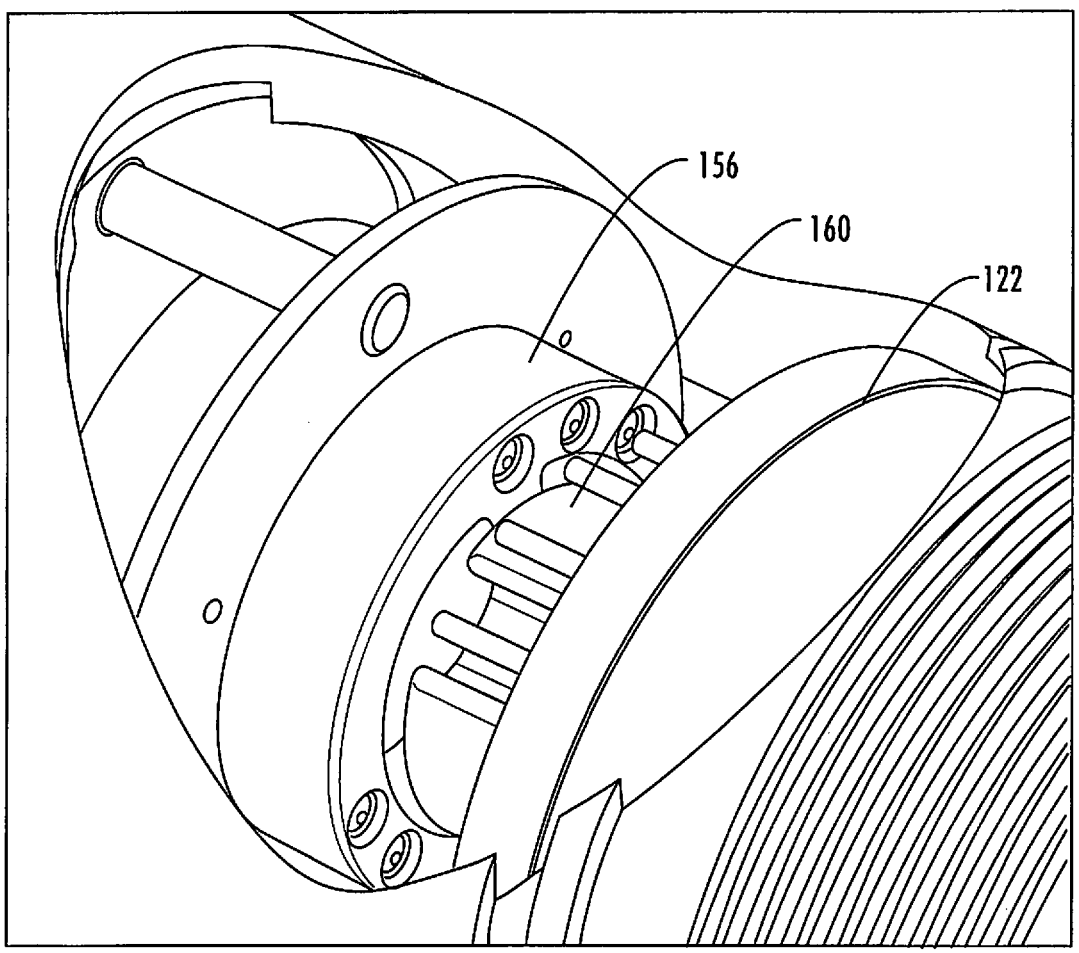
FIG. 9 is a cut-away perspective view of the sensor shown FIG. 4 with a cut-away portion showing the head attachment connector of FIG. 7 abutted with the sensor cartridge of FIG. 6.
Figure 10:
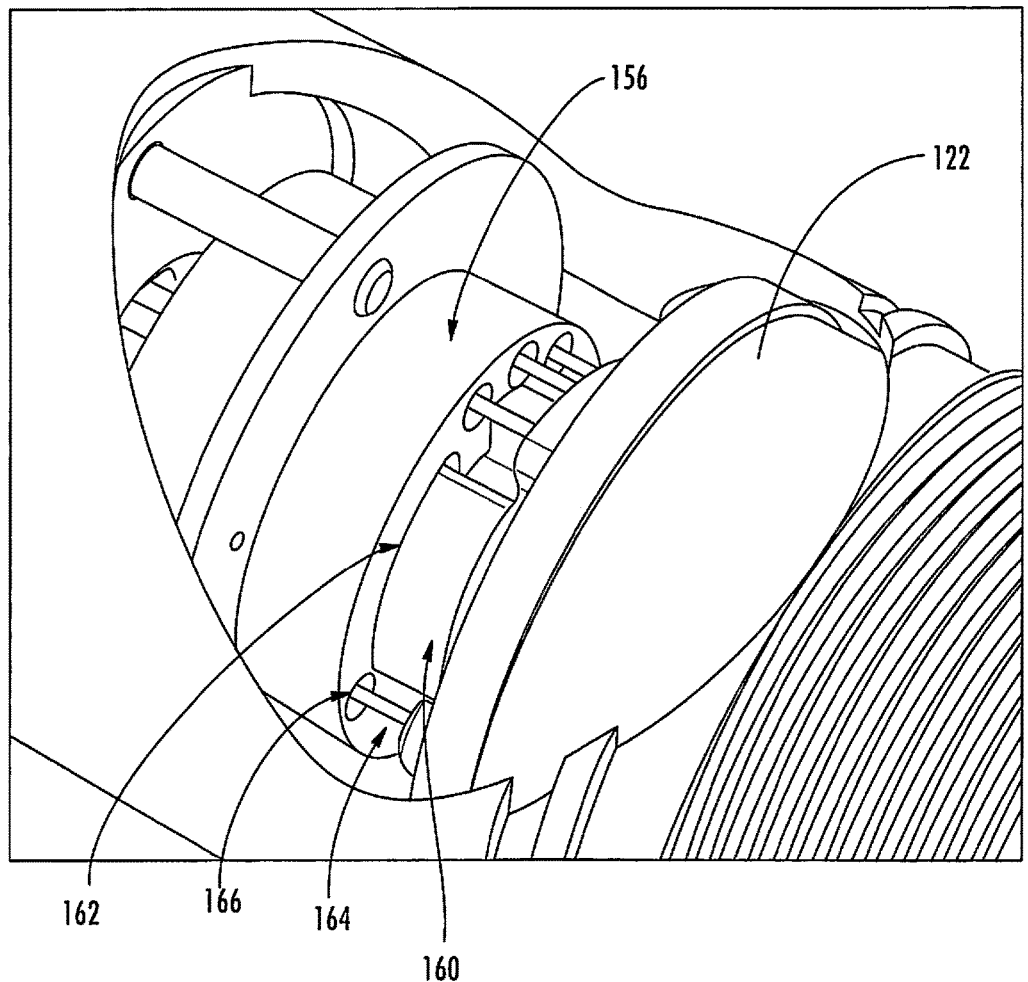
FIG. 10 is a cut-away perspective view of the sensor shown in FIG. 4 with a cut-away portion showing the head attachment connector of FIG. 7 abutted and aligned with the sensor cartridge of FIG. 6.

FIGS. 8, 9, and 10 illustrate the alignment and staging process where the contact members 164, 166 are aligned and joined.

FIG. 8 is a cut-away perspective view of the sensor cartridge 122 received into the sensor head assembly 120 in an initial pre-loaded stage. In the pre-loaded stage, the sensor cartridge 122 is loaded (e.g., inserted or received) within the internal channel 136 and the sensor cartridge 122 is aligned with the sensor head assembly 120 along the longitudinal axis 126. The sensor HAC 120 is recessed by the staging distance 184 within the internal channel 136 from the open distal end 134 of the head assembly 120. The staging distance 184 is a predetermined distance based on the dimensions (e.g., diameter, size, and/or shape) of the sensor cartridge 122 and/or the sensor head assembly 120 such that the sensor head assembly 120 limits angular movement of the sensor cartridge 122 relative to the longitudinal axis 126. In other words, the staging distance 184 is such that a portion of the sensor cartridge 122 resides within head assembly 120 such that the cartridge housing 146 is limited in movement to longitudinal and rotational movement. Limiting angular movement of the sensor cartridge 122 may encourage the contact member 164 to align with the contact member 166. For example, as shown in the illustration, the contact members 164, 166 may require movement along the longitudinal axis 126 in order to mate. As such, movement perpendicular to the longitudinal axis 126 may cause the contact members 164, 166 to misalign and/or may damage the contact members 164, 166.

Additionally, the sensor cartridge 122 has an outer diameter that fits in close tolerance within an inner diameter of the distal end 134 of the sensor head assembly 120, such that when the sensor cartridge 122 is loaded through the distal end 134 into the internal channel 136, the sensor head assembly 120 may also limit angular movement of the sensor cartridge 122 relative to the longitudinal axis 126. In other words, the diameter of the distal end 134 and the diameter of the sensor cartridge 122 are such that when the sensor cartridge 122 is inserted in the internal channel 136, the sensor cartridge 122 is partially limited to travel linearly along the longitudinal axis 126 and rotate about the longitudinal axis 126 (e.g., transverse rotation about the longitudinal axis 126 is substantially eliminated).

FIG. 9 is a cut-away perspective view of the second key component 60 abutted with the sensor HAC 156. As shown in the illustration, the sensor cartridge 122 is received in the internal channel 136 and is aligned along the longitudinal axis 126. However, the second key component 160 and the first key component 162 are not aligned circumferentially. Thus, the contact members 164 and 166 do not engage one another. In other words, the second contact member 164 and the first contact member 166 are longitudinally blocked from engaging one another until the second key component 160 and the first key component 162 interlock and engage one another because the first key component 162 and the second key component 160 extend further toward the sensor HAC 156. In other words, because the key length 194 is greater than the contact length 196, the second key component 160 limits travel of the sensor cartridge 122 along the longitudinal axis 126. As used herein, circumferentially aligned refers to a state where the angular orientation of the sensor cartridge 122 about the longitudinal axis 126 in which the first key component 166 is aligned with the second key component 164.

FIG. 10 is a cut-away perspective view of the sensor cartridge 122 abutted and aligned with the sensor HAC 156 in the intermediate circumferential alignment stage. As illustrated, sensor cartridge 122 is circumferentially aligned with the sensor HAC 156. To circumferentially align the sensor cartridge 122, beginning with the orientation of the sensor cartridge 122 shown in FIG. 9, the sensor cartridge 122 is rotated within the internal channel 136 until the first key component 162 aligns with the second key component 160. When circumferentially aligned, the first contact member 166 is aligned with the second contact member 164.

In the final loaded stage, the first key component 162 and the second component 160 are aligned and engaged with one another, which allows the first key element 192 to engage the second contact member 164 to form an electrical connection. To arrive at the final loaded stage, beginning with the orientation of the sensor cartridge 122 shown in FIG. 10, the sensor cartridge 122 may move along the longitudinal axis 126 until the key components 160 and 162 as well as the contact members 164 and 166 are engaged and interlock. After the final loaded stage, the retaining cap 124 may be used to secure the sensor cartridge 122 to sensor head assembly 120 as described in the discussion of FIG. 4 above.

By practicing one or more of the embodiments described herein, a sensor cartridge 122 may be quickly and safely attached and detached from a sensor head assembly 120.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the subject matter described herein without departing from its scope. While the dimensions and types of materials described herein are intended to define the parameters of the subject matter described herein, they are by no means limiting and are exemplary embodiments. Many other embodiments will be apparent to those of skill in the art upon reviewing the above description. The scope of the subject matter described herein should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the subject matter described herein, including the best mode, and also to enable any person skilled in the art to practice the embodiments of the subject matter described herein, including making and using any devices or systems and performing any incorporated methods. The patentable scope of the subject matter described herein is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A connector mechanism for safely and quickly attaching or detaching a sensor, the connector mechanism comprising:
    a sensor head assembly, comprising:
        a detector body with an internal channel and an open distal end, the internal channel having a longitudinal axis; and
        a sensor head attachment connector (sensor HAC) located within the channel, the sensor HAC oriented to face the distal end, the sensor HAC recessed within the channel remote from the distal end, the sensor HAC including a first electrical connection having at least a first contact member, the sensor HAC including a first key component that is located in a fixed location relative to the first contact member; and
    a sensor cartridge, comprising:
        a cartridge housing that includes a probe component, the cartridge housing configured to be at least partially inserted through the open distal end into the internal channel of the detector body;
        a second electrical connection having at least a second contact member configured to mate with the first contact member; and
        a second key component that is located in a fixed location relative to the second contact member, wherein the first and second key components engage one another before the first and second contact members engage one another,
    the sensor cartridge being configured to be rotated about the longitudinal axis of the internal channel to align the first key component and the second key component with each other; and
    the sensor HAC being recessed within the internal channel by a predetermined distance from the open distal end of the detector body, the predetermined distance being chosen such that the detector body limits angular movement of the sensor cartridge relative to the longitudinal axis of the internal channel when the cartridge housing is at least partially inserted through the open distal end into the internal channel of the detector body.

2. The sensor of claim 1, wherein the second key component is configured to interlock with the first key component, and wherein the first and second contact members are longitudinally blocked from engaging one another until the first and second key components are aligned.

3. The sensor of claim 1, wherein the cartridge housing has an outer diameter that fits within an inner diameter of the distal end of the detector body such that, when the sensor cartridge is loaded through the distal end into the internal channel, the detector body limits angular movement of the sensor cartridge relative to a longitudinal axis of the internal channel.

4. The sensor of claim 1, wherein the second key component extends a key length outward from the cartridge housing, the second contact member extending a contact length outward from the cartridge housing, wherein the key length is greater than the contact length.

5. The sensor of claim 1, wherein the first key component includes a groove and the second key component includes a standoff, and wherein the groove is configured to receive the standoff to enable the first and second contact members to engage one another.

6. The sensor of claim 1, further including a sensor retaining cap, the sensor retaining cap being configured to be mounted to the detector body to retain the sensor cartridge to the sensor head assembly.

7. The sensor of claim 1, wherein the sensor cartridge includes a pre-loaded stage where the sensor cartridge is received in the internal channel and is longitudinally aligned with the sensor HAC.

8. The sensor of claim 1, wherein the sensor cartridge includes an intermediate circumferential alignment stage where the sensor cartridge is received in the internal channel, the sensor cartridge is longitudinally aligned with the sensor HAC, and the first key component and the second key component are circumferentially aligned with each other.

9. The sensor of claim 1, having a final loaded and engaged stage where the first key component and the second key component are aligned and engaged with each other, and where the first contact member and the second contact member are engaged in electrical connection with each other.

10. The sensor of claim 1, wherein the sensor head assembly comprises a third key component that is located in a fixed location relative to the first contact member, the sensor cartridge comprising a fourth key component that is located in a fixed location relative to the second contact member, the third and the fourth key components being configured to engage each other to enable the first and second contact members to engage one another.

11. The sensor of claim 1, wherein the first contact member includes at least one spring-loaded contact element that is configured to engage the second contact member.

12. The sensor of claim 1, wherein the second contact member includes a contact pin.

* * * * *